United States Patent
Pearson

(10) Patent No.: US 7,758,534 B2
(45) Date of Patent: Jul. 20, 2010

(54) TEAR-DUCT DRAIN

(76) Inventor: Andrew Robert Pearson, Pebble Cottage, Milestone Avenue, Charvil, Reading RG10 9TN (GB)

( * ) Notice: Subject to any disclaimer, the term of this patent is extended or adjusted under 35 U.S.C. 154(b) by 189 days.

(21) Appl. No.: 11/695,300

(22) Filed: Apr. 2, 2007

(65) Prior Publication Data

US 2008/0082037 A1    Apr. 3, 2008

(30) Foreign Application Priority Data

Sep. 29, 2006   (GB)   ................... 0619305.6

(51) Int. Cl.
   *A61M 5/00* (2006.01)
   *A61M 25/00* (2006.01)
(52) U.S. Cl. .............. 604/8; 604/264; 604/284
(58) Field of Classification Search ....... 604/4.01–6.16, 604/8–10, 108, 264, 284; 128/151, 152, 128/329, 343, 348–351; 606/108; 623/4.1
   See application file for complete search history.

(56) References Cited

U.S. PATENT DOCUMENTS

| | | | | |
|---|---|---|---|---|
| 3,871,380 A | * | 3/1975 | Heros | 604/264 |
| 4,695,275 A | * | 9/1987 | Bruce et al. | 604/264 |
| 6,149,684 A | * | 11/2000 | Herrick | 623/4.1 |
| 6,406,453 B1 | * | 6/2002 | Goode et al. | 604/8 |
| 2002/0032400 A1 | | 3/2002 | Moazed | |
| 2006/0100700 A1 | * | 5/2006 | Bernard et al. | 623/4.1 |
| 2006/0276738 A1 | * | 12/2006 | Becker | 604/8 |

FOREIGN PATENT DOCUMENTS

| | | |
|---|---|---|
| GB | 2273243 A | 6/1994 |
| GB | 2273243 A | 6/1994 |
| WO | WO98/33461 | 8/1998 |
| WO | 2006133066 A2 | 12/2006 |

OTHER PUBLICATIONS

Patent Act 1977: Search Report Under Section 17 for GB0619305.6 dated Dec. 22, 2006.
International Search Report dated Dec. 10, 2007, for corresponding International Application No. PCT/GB2007/003408.

* cited by examiner

*Primary Examiner*—Leslie R Deak
*Assistant Examiner*—Philip R Wiest
(74) *Attorney, Agent, or Firm*—Heslin Rothenberg Farley & Mesiti P.C.; Victor A. Cardona, Esq.

(57) ABSTRACT

A tear-duct drain includes a hollow rigid tube which is elongated and has a first flange at one extremity thereof. A flexible, resilient and collapsible second flange is bonded to the tube at a predetermined distance away from, and so providing a leading edge at, the opposite extremity of the tube.

23 Claims, 6 Drawing Sheets

Figure 1:
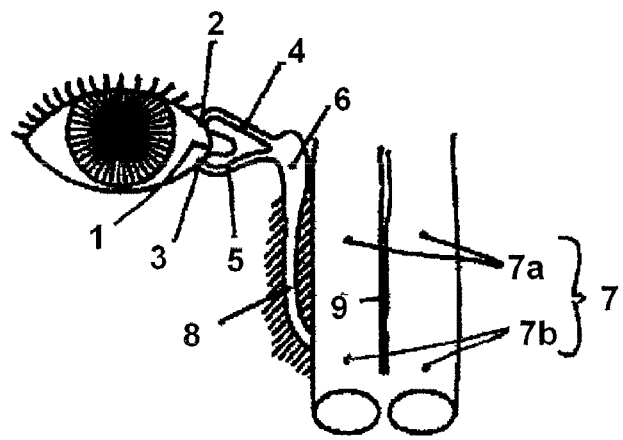

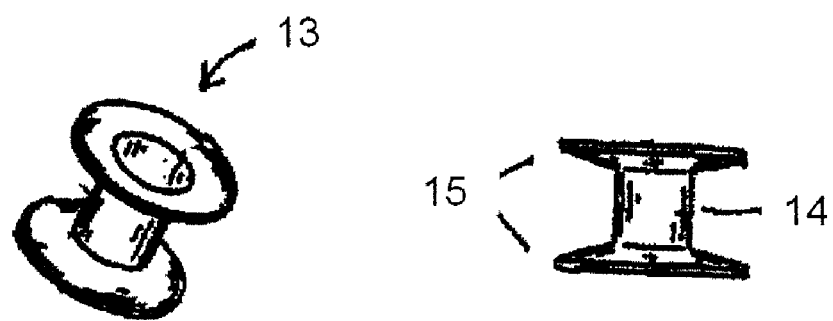
FIG. 4A (Prior Art)
FIG. 4B (Prior Art)
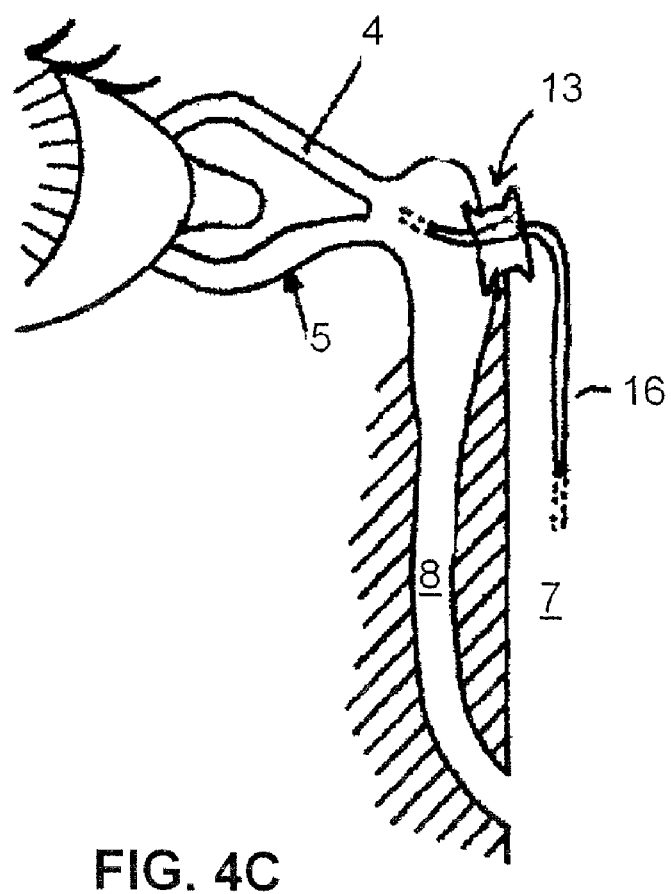
FIG. 4C (Prior Art)

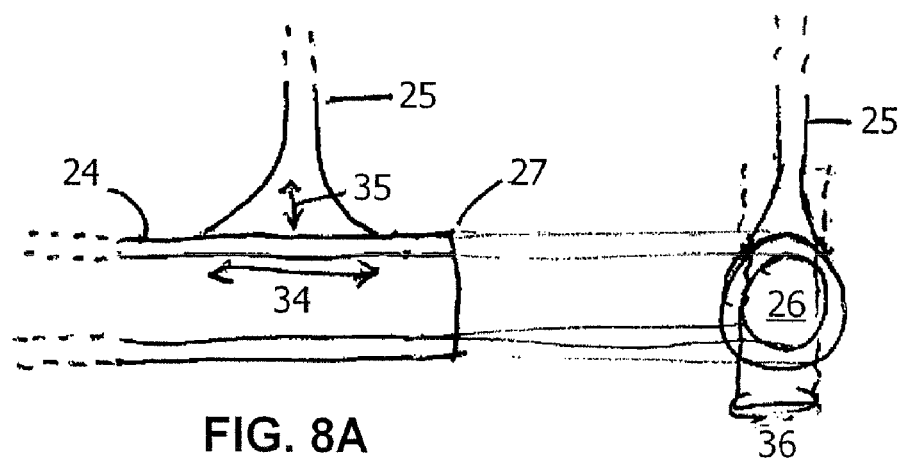
FIG. 8A
FIG. 8B
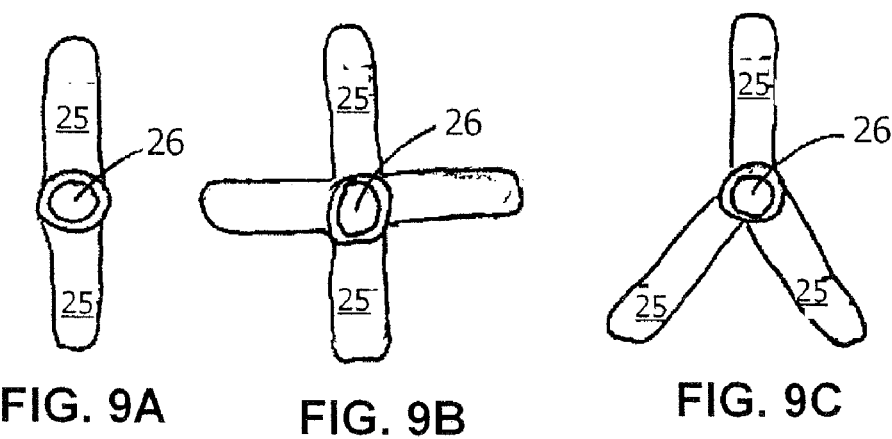
FIG. 9A  FIG. 9B  FIG. 9C
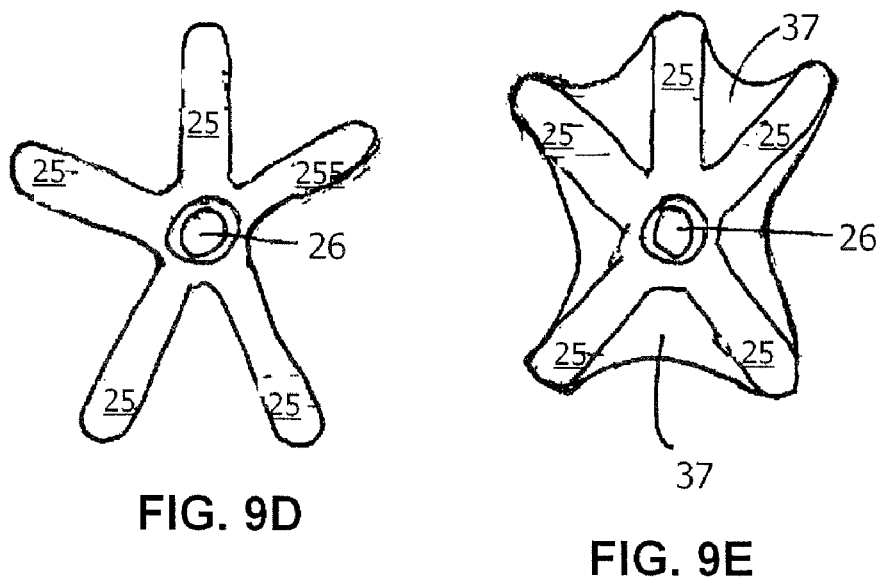
FIG. 9D
FIG. 9E

TEAR-DUCT DRAIN

CROSS REFERENCE TO RELATED APPLICATIONS

This application claims priority from United Kingdom Application No. GB0619305.6 filed on Sep. 29, 2006, the entire disclosure of which is incorporated herein by reference.

TECHNICAL FIELD

The present invention relates to a medical device that has its main application in corrective tear-duct surgery. The improvements provided by the device greatly help to overcome the numerous disadvantages of previous approaches in this field.

BACKGROUND OF THE INVENTION

In healthy individuals, tear fluid (that is "lacrimal" fluid) is normally supplied continuously to their eyes from lachrymal glands, each being located in a lateral and superior relation to the respective eye. Upper lacrimal ducts feed the fluid from each gland to a respective conjunctival sac, in which the relevant eyeball is partially encased. The lacrimal fluid subsequently washes the sclera and other conjunctival components of the eye, as well as its cornea.

Under such healthy conditions, excess lacrimal fluid that cannot be retained by each eye and conjunctiva tends to be drained (see FIG. 1 of the drawings accompanying this specification) from the inner-canthus 1 (at the corner of the eye) to the nasal passages 7a, b, in particular to the inferior nasal meatus 7b.

After any excess fluid has drained from the inner-canthus 1, it passes through a network of passages commencing with the puncta, which are seen as small papillae 2, 3 adjacent to the inner-canthus 1. From here, the lacrimal fluid is subsequently collected in the lacrimal sac 6, which is connected to the puncta via a number of canaliculi 4, 5. The lacrimal fluid is thereafter drained through the nasolacrimal duct 8 into the interior meatus 7b of the nose.

Sometimes, if an unwanted closure of the passageways of the system occurs, for example by way of a blockage of any one of its sub-components, excess lacrimal fluid can no longer be disposed of in the usual way. Such a blockage can result from, inter alia, congenital anomalies, accidents, inflammation, advancing age, and so forth, and tends to cause the eye to continuously brim over with tears, with concomitant discomfort to the individual.

More seriously, if the blocked tears stagnate, they can become infected, which can then lead to inflammatory irritation of the mucous membranes of the affected passage. In turn this can result in proliferation of local epithelium, as well as hyperaemia, and even a purulent exudation into the conjunctiva. Infection caused in this way can ultimately lead to scarring over of the canaliculi 4,5.

In severe cases, the resultant permanent closure can require a corrective surgical procedure known as a dacryocystorhinostomy (DCR). In some of these cases, only the defective portion of the lacrimal drainage system needs to be reconstructed. Thus, if the sole blockage occurs in, for example, the nasolacrimal duct, the latter can be removed, and the remaining lacrimal sac cavity can then be joined directly with the mucosa of the nasal fossa. This is typically achieved by removing tissue, including the intervening segment of nasal bone and periosteum, so that the drainage of tear liquid into the nose can be more or less restored.

In many other cases, however, removal of the entire lacrimal drainage system may be necessary, the insertion of a replacement mechanical device (for example a tube) then being required. Such operations have to date seldom been entirely successful, because at least the following two particular difficulties have typically been experienced.

Firstly, as the nasal bone heals around the lower end portion of the inserted replacement tube, the latter is gradually rejected from the bone and flesh of the patient. And secondly, the patient's flesh also tends to heal over the external end of the replacement tube at the inner-canthus 1, which therefore requires appropriate surgical reopening from time to time.

Conventionally, the replacement tube utilised in tear-duct surgery has been a small tube constructed of Pyrex™ glass, stiff plastic or some other relatively rigid material. However, usually it is Pyrex™-type glass that has been preferred, since this can neither be destroyed, nor corroded or otherwise affected by a patient's bodily fluids.

These tubes of Pyrex™ glass are generally known by surgeons as "Lester Jones" tubes, being named after their designer, Mr Lester T Jones, and are sometimes simply referred to as "Jones" tubes. Very similar devices go by the alternative trade names "Callaghan Cox", "Gladstone Putterman", "Baylis", and "Naugle" tubes. These replacement tubes have a typical length of the order of about 18 mm and, as such, are inserted into the inner corner of the eye, and then down the surgically created passage, so as to allow the drainage of the excess lacrimal fluid internally into the nose.

Despite their rigidity, the main flaw of these replacement Jones-type tubes is that, as described above, they usually tend to be worked out of their in situ position by the action of the patients' own bone and flesh. They are therefore at risk of being completely lost either by descending into the nasal passage or by ascending into the eye. In either eventuality, the function of these replacement tubes is of course utterly negated, consequently necessitating the inconvenience and cost of one, or more, further corrective operations.

In addition, double-flanged Jones-type tubes have also been previously made available. These have two opposing flanges at either end of a hollow shank, with the aim of attempting to prevent their rejection. However, these tubes tend not to be particularly effective either since, in practice, they have at least the following extra disadvantages:

a) The relatively larger diameter of their additional leading (internal) flange of rigid glass, as compared to that of their hollow shank, means that these tubes are relatively very difficult to place in situ. This is because the surgically created passage is more difficult to open and traverse by a large leading flange.

b) Further, a large leading flange requires either a correspondingly larger surgically passage to be created before the tube's insertion, or if the flange is pushed through an otherwise smaller passage, damage to the tissue surrounding the passage is likely to create a larger diameter through the passage. Hence, when the tube has been placed in situ, its shank will be inherently less stable.

c) The diameter of the rigid internal flange is nevertheless still relatively small compared to that of the passage after its insertion and so little barrier to the extrusion of the in situ tube is thereby provided.

d) This leading flange is furthermore positioned at a relatively sub-optimal site along the shank, being right at its internal tip and, therefore, after insertion the orifice at this tip is prone to blockage by the normal growth of the nasal mucosa that closely surrounds it.

Figure 2:
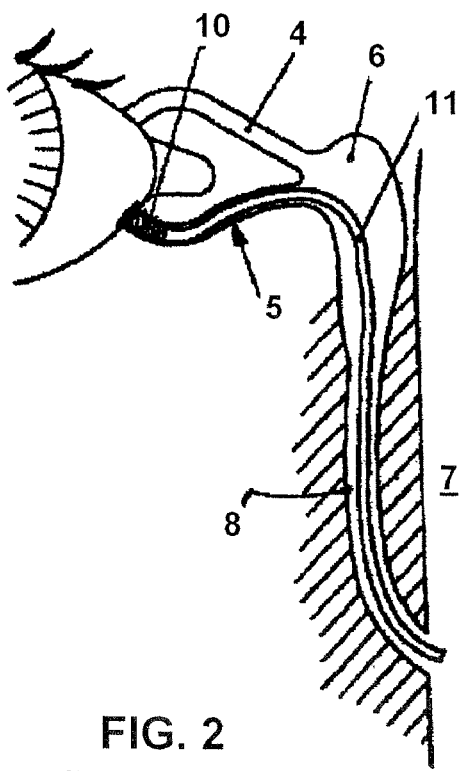
Figure 3:
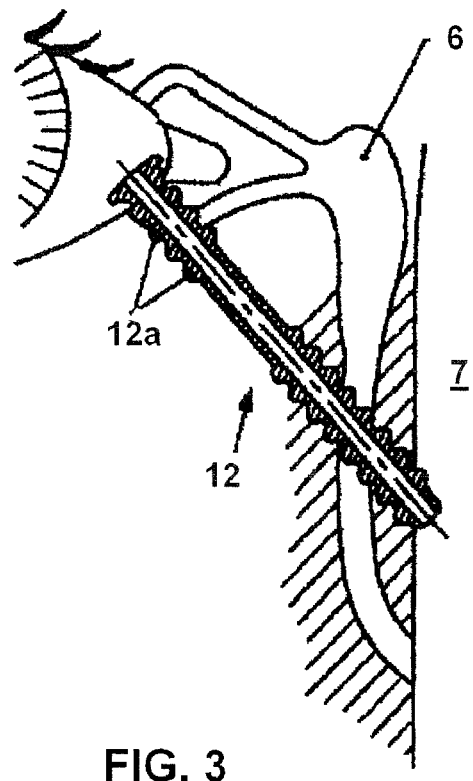

Other prior devices include those as follows:

FR-A-2, 813, 522 (see FIGS. 2 and 3 accompanying the present specification) discloses the use of a tubular lacrimal drain 11, 12 having one or more parts, one of which is an internal fixing unit. This allows anchoring of the drain 11,12, typically by providing a screw-threaded attachment means 10, 12a.

CN-A-1, 650, 824 also provides an artificial tear duct, in this case being in the form of a spiral spring-like structure, typically used as a temporary stent to allow scar tissue to become stable before the spring is softened and thereafter pulled out as an unravelled metal wire.

U.S. Pat. No. 5,062,831 (see FIGS. 4A-C accompanying this present specification) discloses the use of a solid tubing 16, having no lumen, for temporarily removing excess lacrimal fluid by capillary action. A conventional DCR is performed, by removing adjacent bone so that the remaining sac communicates with the internal nasal meatus 7. A catheter 13, with enlarged portions 15 at either end of an elongate shank portion 14, is used simply as a temporary stent to prevent scarring over of the newly opened hole between the sac and the nose.

This procedure, whilst being a suitable treatment for nasolacrimal duct 8 obstruction, cannot assist canalicular 4, 5 obstruction surgery. This is, firstly, because no external opening on the corner of the patient's eye is made. And, secondly, even if it were to be made, the internal opening created by the DCR is kept overly large by the similarly large diameter of the catheter's shank portion 14, which in any case creates a degree of instability. Understandably, the use of such a catheter 13 is taught purely as being a temporary measure.

Figure 5A:
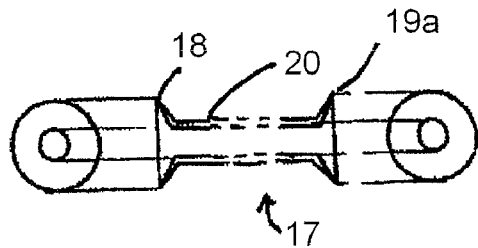
Figure 5B:
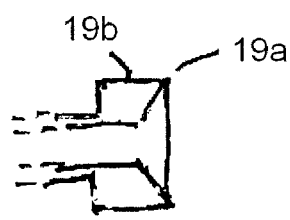
Figure 5C:
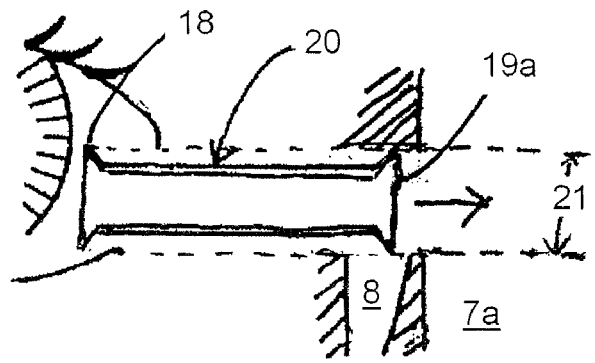
Figure 5D:
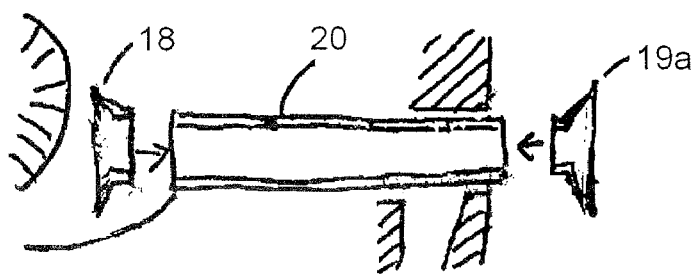
Figure 5E:
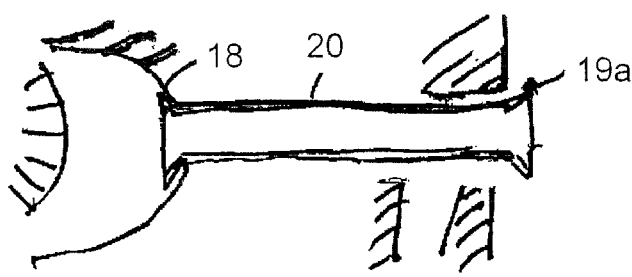

JP-A-2004-230, 012 (see presently accompanying FIGS. 5A-C) discloses a tear duct stent 17 that has enlarged portions (or collars) 18; 19a, 19b at either end of a tube 20. Hence, this stent is similar in shape to the above-described double-flanged Jones tube, but because this stent is formed of a soft material, the length of its tube can be adjusted as required by cutting it with scissors. Further, having been placed in situ, one or more of its collars may subsequently be cut away to allow the remainder of the stent to be pulled and so removed.

Because of its enlarged ends, insertion of the device can again be problematic, as with the double-flanged Jones-type tubes. Also, the creation of a tissue passage lumen of relatively larger diameter 21 than that of their tube itself may occur, so that in situ instability can once again be a problem.

Moreover, temporary removal of these stents does not appear to be possible, and is not taught in JP-A-2004-230, 012. Indeed, its teaching appears to suggest that the device 17 can be constructed in situ, for example by bonding either (or both) collars 18; 19a, 19b to an already inserted tube 20. Even this would seem to be manually difficult and, potentially, impractical.

The present invention aims to provide an improved device for correcting tear-duct obstructions and, in particular, for the correction of canalicular obstructions. The latter have previously tended to be even less successfully treated than blockages of other tear-duct system parts.

The device of the present invention has the advantages that it can be more accurately placed in situ and with greater ease than previous devices, as well as being able to be left more stably in situ afterwards. This befits the relatively more permanent correction that it can provide, if such permanency is required.

Potentially permanent devices of this type also need to be easily removeable, at least temporarily, so that they can be cleansed along with the patient's consequently vacated tissue passageway. This helps to avoid, for example, microbial contamination, so that tissue damage resulting from inflammation is less likely to occur. If left unchecked, however, such damage would tend to increase the likelihood of rejection of the device from the patient.

The elongated tube of each of these improved devices may be made of any suitably inert material that promotes a high level of biocompatibility with patient tissue, as well as the preferred ease of cleaning the device as a whole upon its temporary withdrawal.

Whilst the tube of the present device has a first enlarged external portion at one end that is designed to act as an anchor at the corner of the patient's eye, it also has a collapsible second flange that is preferably positioned towards the opposite end of the tube. Because of its resilience and, typically, relatively large diameter, this second flange tends to prevent the device from slipping. This is because it helps to secure the tube in its in situ position, and so stabilise it against any forces (for example during sneezing of the nose or blinking of the eye) that it might experience thereafter. This is effected by the opening-up of the flexible flange inside the patient's nose and its subsequent positioning against the nasal mucosa around the internal opening of the tissue passageway.

Preferably, the flexible material of which the collapsible second flange is constructed has a relatively much smaller dimension of thinness compared to that of the diameter of the elongate tube. As such, when the device is being inserted, or being temporarily withdrawn, this second flange is consequently encouraged by the surrounding tissue of the passageway to flex. Thus, it can lie flush against the body of the tube, and to the appropriate side of the site of its bonding to the tube, depending upon the relative direction of movement of the tube.

This helps to reduce as much as possible any increase in effective total diameter that is presented by the drain, in terms of the combined cross-section of both its tube and its flush second flange, as it is passed through the patient's tissue. In particular, the tube may be indented on either side of the site of bonding to provide recesses (in the tube's surface) that can accommodate the second flange when flexed.

During the device's insertion, and any temporary withdrawal, the risk of either damage to the device, or traumatisation of the patient's tissue, can thus be minimised. Removal of the device, as frequently as is needed, is facilitated therefore allowing it to be cleansed according to each patient's needs. No matter how often such removal is performed, damage to tissue is minimised, which in turn helps to maximise the long-term stability of the device when it is left in situ.

The present invention will now be described, in a non-limiting way, by the following preferred examples with reference to, and as illustrated in, the accompanying figures, in which:

FIG. 1 schematically illustrates the functional anatomy of a normal and healthy tear-duct system;

FIGS. 2-5 depict known devices attempting, as described above, to correct various obstructions of unhealthy tear-duct passages;

FIGS. 6A-D show an improved device according to one embodiment of the present invention;

FIGS. 7A-D illustrate an improved device according to a further embodiment of the present invention;

FIGS. 8A-B show an enlarged view of one embodiment of the device of the present invention, in which the site of bonding of the second flange to the tube is schematically highlighted; and, FIGS. 9A-E depict some variations of possible shapes for the second flange of the device of the present invention.

Figure 6A:
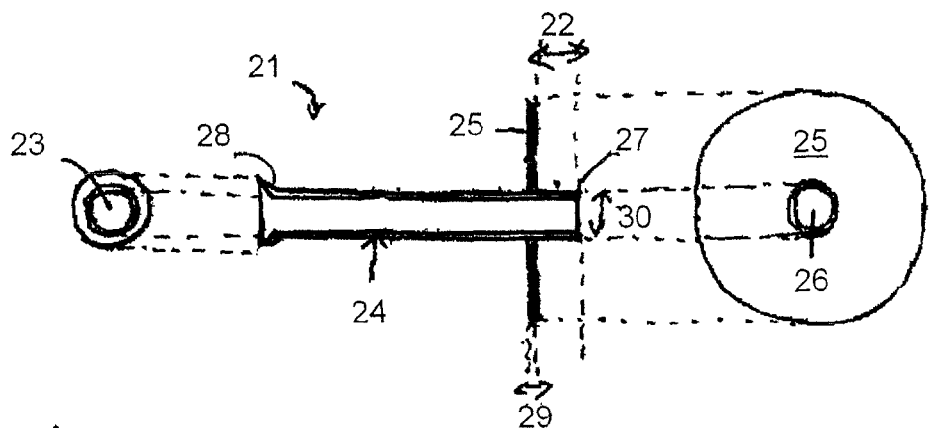

The tear-duct drain 21 shown in FIG. 6A has a first flange 28 at the external (that is, inner-canthal) opening 23 of its tube 24. A second flange 25 is also provided and is positioned close to—but not at—the internal (that is, nasal) opening 26 of the leading edge 27 of the tube 24.

Preferably, the tube 24 and first flange 28 are composed of a rigid material, for example a glass or a plastics material. Glass is generally a preferred material, since it has excellent capillary characteristics and is very biocompatible.

The relative dimensions, and relative resilience, of the second flange 25 are predetermined to allow the tube 24, when in situ, to be stable to any potentially destabilising forces that might otherwise cause either its movement inwards into the nose or outwards towards the eye. Patients are therefore provided with a significant safety benefit to their eyes. Complete loss of the device 21 is also reduced.

The relative resilience of the second flange 25 can be defined in terms of the degree of the relative shear forces involved. That is, for example, the maximum shear force that the flange 25 can withstand before it collapses; and, the respective minimum that it can overcome before it bounces back into shape.

The flexibility of the second flange 25 also ensures that it can collapse in both directions. That is, both: (i) towards the external end 28 of the tube 24 [a "first flush position"]; and, (ii) towards the leading edge 27 of the tube 24 [a "second flush position"]. The position adopted depends upon the direction in which the tube is being urged by the surgeon.

Figure 6B:
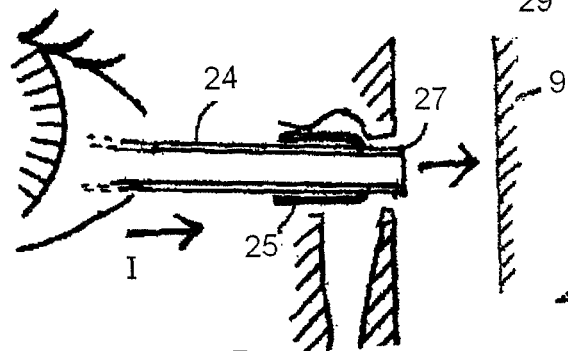

The second flange 25 can thus adopt the first flush position during the tube's insertion (that is, in direction I, as shown in FIG. 6B). Once the internal end of the tube 24 reaches the space just beyond the entrance to the inside of the nose, the resilience of the second flange 25 enables it to spring open. Thus, somewhat in the manner of an umbrella, it can change its configuration from being folded into being in an open position. This springing open can if necessary be facilitated by the surgeon, for example by applying a degree of manual pressure against the elasticity of the tissue area surrounding the nasal (inner) orifice of the lumen of the passageway, so as to aid release of folded flange into nasal meatus 7.

Subsequent fixing of the tube 24 into its secured, in situ position is encouraged by the resilient nature of the opened internal second flange 25 and its typically substantially larger diameter, as compared to that of the inner orifice. This is further encouraged when the device 21 is slightly withdrawn back towards the eye (that is, in the opposite direction to direction I in FIG. 6B), so that the second flange 25 abuts against the tissue surrounding the inner orifice.

Figure 6C:
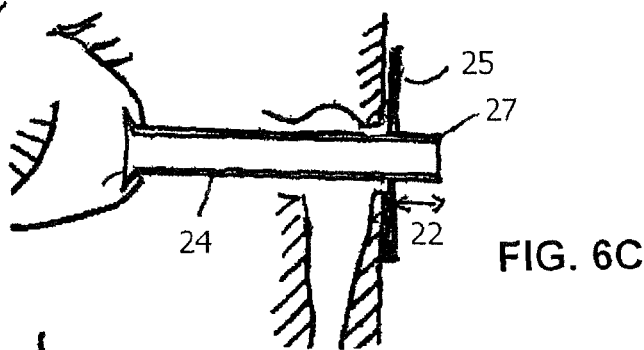
Figure 6D:
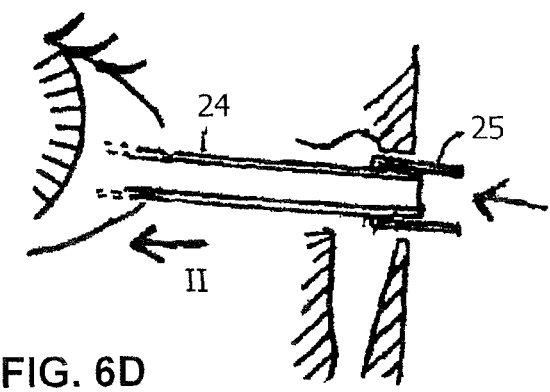
Figure 7A:
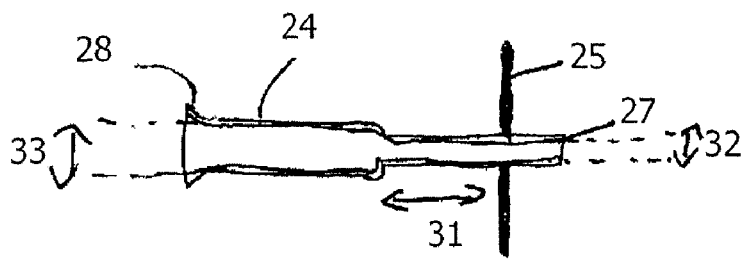
Figure 7B:
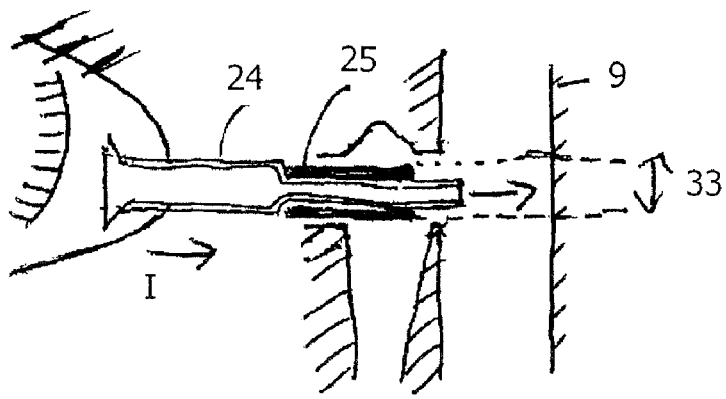
Figure 7C:
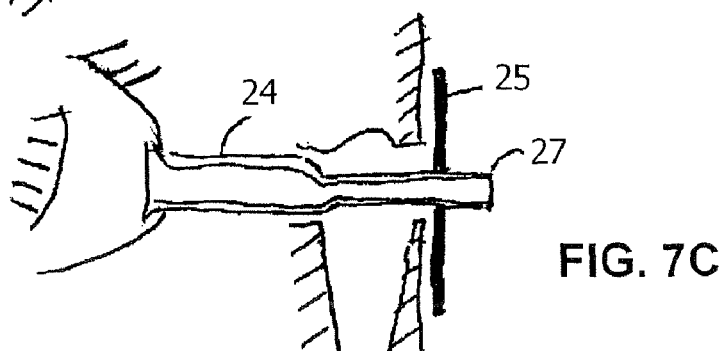
Figure 7D:
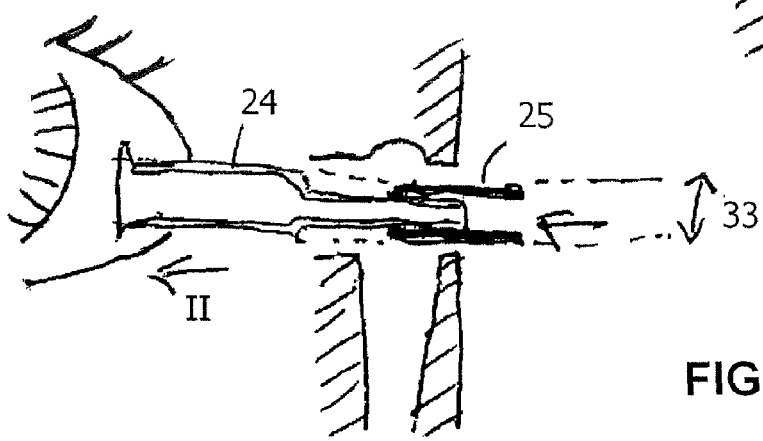

Moreover, maintenance of this secure fixing is also encouraged by minimising any potential increase in the diameter of the passageway, that might otherwise be caused by trauma to the patient's tissues both during initial placement and during temporary withdrawal of the device (in direction II as shown in FIG. 6D). This is achieved by ensuring that the thickness 29 of the flange 25 is relatively small compared to the cross-sectional diameter 30 of the tube 24. In other words, by minimising the total cross-sectional diameter of the device 21 with the second flange 25 collapsed in its first flush position.

As shown in FIGS. 7A-D, such minimisation can optionally be achieved by adapting the tube's shape to include indentations on either side of the bonding site of the second flange, which can therefore adopt the flush positions by collapsing into and thus being held in the recesses (for example, 31) so created.

The collapsible flange is typically bonded to the inert material of the tube 24 by a suitable adhesive. For example, any glue that can bond potential collapsible flange 25 material, such as silicone, to the material of the tube 24, for example glass, can be used. The chosen glue should also preferably be able to withstand high temperatures for autoclaving, as well as being generally tissue biocompatible.

The shape of the flange 25 at its site of bonding to the tube may be splayed to allow greater strength. Thus, for example, as shown in FIG. 8 (for one non-limiting embodiment) the splaying 34, 35, 36 may advantageously allow the flange 25 to have a greater surface area that can be adhered to the tube 24.

As mentioned, the bonded second flange 25 can be made of any appropriately flexible material that retains its memory after deformation, such as, for example a silicone or a rubber, or indeed alternatively any suitable plastics material.

The exact shape of the second flange 25 can be chosen to suit the needs of each specific patient and so it need not necessarily be circular (as shown in FIG. 6A) in cross-section.

Thus, further non-limiting examples of the many different types that can be appropriately utilised are shown in FIGS. 9A-E. In particular, if the second flange 25 comprises a plurality of arms radiating from the central lumen 26, it is preferable that an odd number of arms are incorporated. This allows the arms to fold into a more compact arrangement as the flange 25 collapses, thus minimising the cross-sectional diameter of the device 21 as it is inserted into place or temporally withdrawn for cleaning. Additionally, the outer circumferential profile of the second flange 25 is preferably as uniformly smooth as possible, for example any arms should preferably have rounded extremities.

Importantly, the second flange 25 is pre-bonded at a predetermined set distance 22 from the internal end 27 of the glass tube 24, and so the clinician need not actually bond the second flange 25 to the tube 24 at any stage. Further, the glass tubes are also typically manufactured to predetermined lengths, so that, the length required to match each patient's anatomy can be chosen by the surgeon before the corrective procedure is commenced.

As noted above, many of the previously known devices appear to have been designed for insertion solely as a temporary measure after surgery and, as such, they are used simply to keep an artificially created passageway open for long enough for the patient's surrounding tissues to heal. Often known as "stents", these devices are removed once the appropriate number of weeks or months, after the surgery, have elapsed. In addition, almost all are usually inserted through at least a remaining part of the patient's own lacrimal apparatus that has retained some workable function.

By contrast, the improvements provided by the device 21 of the present invention allow it to be inserted, if necessary, as a relatively permanent system, often as an independent bypass of a patient's natural tear-duct system. The chosen parameters of the device 21 and particularly those of its second flange 25, greatly enhance its ability to efficiently provide this permanent type of treatment, by avoiding counter-productive complications (such as inflammation of the nearby tissues, and so forth) that, as mentioned above, might otherwise arise.

In use, as also indicated above, the present device 21 is particularly suited to correction of canalicular obstructions. Once the clinician has surgically created the appropriate bypass tissue passage into the nasal meatus 7, the device 21 can easily be placed into the correct in situ position (as shown in FIG. 6C). By making use of the slight elasticity of the intervening tissue, this can be achieved by inserting it inwardly into the passage (see FIG. 6B) until the leading edge 27 of the tube is sufficiently inside the nasal meatus 7. This allows the internal second flange 25 to have already flexibly opened out due to its inherent resilience. The device 21 can then be withdrawn slightly until the opened second flange 25 abuts the nasal mucosa surrounding the internal orifice of the bypass passage. The positioning of the internal second flange 25, and thus the in situ placement of the device 21 as a whole, can therefore be accurately controlled by the clinician.

The bonding of the second flange 25 to the tube 24 at a predetermined distance from the internal end 27 of the tube, ensures that a section 22 of the tube is proud of the second flange 25. Being proud, its obstruction (for example by the formation of scar tissue from the nasal mucosa) is much less likely when it is in situ, so helping to promote a more continuous drainage of the excess lacrimal fluid.

Devices according to the present invention may, of course, differ in their absolute dimensions from case to case, with these being specifically chosen so as to maximise the above-described advantages for each individual patient.

Purely as a way of illustrating this specificity in a non-limiting manner, in one embodiment of the present invention, the outer diameter of the first, rigid flange 28 might be chosen to be between about 3 to 4 mm, whilst that of the tube 24 would then suitably be about 2-2.5 mm. In such a case, the diameter of the second flange 25 would typically be of the order of 7.5 mm or less, and preferably about 5 mm. Its thickness 29 would consequently be of the order of 1 mm or less, and the tube's proud section 22 would also generally have a chosen length of about 1 mm.

The dimensions of any recesses 31 as mentioned above—for example see FIG. 7—can also be varied to accommodate the associated dimensions chosen for the second flange 25. Alternatively, portion of the tube 24 adjacent to the edges of the flange 25 can be raised slightly to provide support.

In conclusion, the advantages of the improved device according to the present invention, as compared to known devices, include the following.

It is simpler to insert, especially compared to devices having an enlarged flange as their leading edge. The large internal flange provides the much greater stability in situ that is required for a permanent device. Moreover, because its leading edge also provides in situ a set length of tube that is proud inside the nasal meatus, obstruction of the internal orifice of its lumen is much less likely.

It can also be readily removed on a temporary basis to allow its regular cleaning and, following its reinsertion, any risk of it falling out thereafter is minimised.

In order to remain securely in situ, the device does not depend upon gravity, by having the relatively large weight flanges that are used in some known devices.

The device also does not rely upon its tube having to be cut to size or glued during its insertion, or its flanges being cut off to allow its withdrawal.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A tear-duct drain configured to extend through a surgically-created tissue passage between an eye and a nasal meatus of a patient, to promote drainage of excess lacrimal fluid, the drain comprising: (a) a hollow rigid tube being elongate and having a first flange at one extremity, the tube being of substantially uniform diameter along its length; and (b) a flexible, resilient and collapsible second flange, being bonded to said tube at a predetermined distance away from an opposite extremity of said tube to ensure that a section of said tube is proud of said second flange, the tube and the first flange consisting of a rigid material, and the second flange consisting of a flexible material, the rigid material and the flexible material being different materials, the tube having a length chosen to match the patient's anatomy, the length of the tube between the first flange and the second flange being substantially equal to the length of the tissue passage.

2. The tear-duct drain as claimed in claim 1, wherein said second flange has a relatively smaller predetermined thinness, in a direction parallel to that of the elongation of said tube, compared to the cross-sectional diameter of said tube; whereby a ratio is minimized of: (i) the cross-sectional diameter of the total of both the tube together with the second flange, when flush against said tube, to (ii) the cross-sectional diameter of said tube alone.

3. The tear-duct drain as claimed in claim 1, wherein said second flange has a relatively greater diameter than that of said first flange.

4. The tear-duct drain as claimed in claim 1, wherein said drain comprises a biologically inert material.

5. The tear-duct drain as claimed in claim 1, wherein said tube and said first flange comprise a rigid material selected from the group consisting of glass and plastics materials.

6. The tear-duct drain as claimed in claim 1, wherein said second flange has a predetermined resilience allowing it a flexibility to deform during placement and removal, yet allowing it an in situ rigidity to resist such deformation.

7. The tear-duct drain as claimed in claim 1, wherein said second flange comprises a biocompatible material selected from the group consisting of silicone and soft plastic materials.

8. The tear-duct drain as claimed in claim 1, wherein the cross-sectional shape of the second flange comprises a plurality of arms.

9. The tear-duct drain as claimed in claim 8, wherein said plurality of arms comprises an odd number of arms, each arm being interconnected by a predetermined thickness of material.

10. A tear-duct drain configured to extend through a surgically-created tissue passage between an eye and a nasal meatus of a patient, to promote drainage of excess lacrimal fluid, the drain comprising: (a) a hollow rigid tube, being elongate and having a first flange at one extremity; and (b) a flexible, resilient and collapsible second flange, being bonded to said tube at a predetermined distance away from an opposite extremity of said tube to ensure that a section of said tube is proud of said second flange, the proud section of the tube being of uniform diameter, the tube and the first flange consisting of a rigid material, and the second flange consisting of a flexible material; wherein said hollow tube and said first flange comprise a material selected from the group consisting of rigid glass and rigid plastics material, the rigid material and the flexible material being different materials, the tube having a length chosen to match the patient's anatomy, the length of the tube between the first flange and the second flange being substantially equal to the length of the tissue passage.

11. The tear-duct drain as claimed in claim 10, wherein said second flange has a predetermined resilience allowing it a flexibility to deform during placement and removal, yet allowing it an in situ rigidity to resist such deformation.

12. The tear-duct drain as claimed in claim 10, wherein said second flange comprises a biocompatible material selected from the group consisting of silicone and soft plastic materials.

13. The tear-duct drain as claimed in claim 10, wherein the cross-sectional shape of the second flange comprises a plurality of arms.

14. A tear-duct drain configured to extend through a surgically-created tissue passage between an eye and a nasal meatus of a patient, to promote drainage of excess lacrimal fluid, the drain comprising: (a) a hollow rigid tube, being elongate and having a first flange at one extremity; and (b) a flexible, resilient and collapsible second flange, being bonded to said tube at a predetermined distance away from the opposite extremity of said tube to ensure that a section of said tube is proud of said second flange, the proud section of the tube being of uniform diameter, the tube and the first flange consisting of a rigid material, and the second flange consisting of a flexible material; the rigid material and the flexible material being different materials; wherein said tube and said first flange comprise a rigid material selected from the group consisting of glass and plastics materials; and wherein said second flange has a predetermined resilience allowing it a flexibility to deform during placement and removal, yet allowing it an in situ rigidity to resist such deformation, the tube having a length chosen to match the patient's anatomy, the length of the tube between the first flange and the second flange being substantially equal to the length of the tissue passage.

15. The tear-duct drain as claimed in claim 14, wherein said second flange comprises a biocompatible material selected from the group consisting of silicone and soft plastic materials.

16. The tear-duct drain as claimed in claim 14, wherein the cross-sectional shape of the second flange comprises a plurality of arms.

17. The tear duct drain as claimed in claim 14 wherein the second flange, when in its unflexed position, extends in a substantially radial plane.

18. A tear duct drain configured to extend through a surgically-created tissue passage between an eye and a nasal meatus of a patient, to promote drainage of excess lacrimal fluid,comprising: (a) a hollow rigid tube, being elongate and having a first flange at one extremity, the tube being of substantially uniform diameter along its length, the first flange being a continuous peripheral rigid flange; and (b) a flexible, resilient and collapsible second flange through which the tube passes, bonded to said tube adjacent to the opposite extremity of said tube, the tube and the first flange being composed of a rigid material whereas the second flange is composed of a flexible material, the rigid material and the flexible material being different materials, the second flange being sufficiently thin to flex back and lie substantially flush against the outside of the tube during insertion of the drain into the surgically-created tissue passage in the patient, and being sufficiently resilient to return to its unflexed position when in the nasal meatus, the tube having a length chosen to match the patient's anatomy, the length of the tube between the first flange and the second flange being substantially equal to the length of the tissue passage.

19. A tear duct drain as claimed in claim 18 wherein the second flange, when in its unflexed position, extends in a substantially radial plane.

20. A tear duct drain as claimed in claim 18 wherein the diameter of the second flange is greater than that of the first flange.

21. A tear duct drain as claimed in claim 18 wherein the rigid tube defines at least one indentation adjacent to the second flange into which the second flange locates during insertion of the drain.

22. A tear duct drain as claimed in claim 18 wherein the second flange is circular.

23. A tear duct drain as claimed in claim 18 wherein the second flange defines a plurality of radiating arms.

* * * * *